United States Patent [19]

Lamers

[11] Patent Number: 5,736,153
[45] Date of Patent: Apr. 7, 1998

[54] PLASTER WITH A SUPPLY OF A MEDICALLY ACTIVE SUBSTANCE

[75] Inventor: Jacobus Stephanus Lamers, Bemmel, Netherlands

[73] Assignee: Lamers Beheer B.V., Gendt, Netherlands

[21] Appl. No.: 428,163

[22] PCT Filed: Oct. 26, 1993

[86] PCT No.: PCT/NL93/00216

§ 371 Date: Jun. 15, 1995

§ 102(e) Date: Jun. 15, 1995

[87] PCT Pub. No.: WO94/09735

PCT Pub. Date: May 11, 1994

[30] Foreign Application Priority Data

Oct. 27, 1992 [NL] Netherlands .......................... 9201864

[51] Int. Cl.$^6$ .......................... A61M 37/00; A61K 9/70; A61F 13/02
[52] U.S. Cl. .......................... 424/449; 604/87; 604/306; 604/307; 206/441; D24/189
[58] Field of Search .......................... 424/449; 602/54, 602/46, 52; 222/81, 83, 85; 604/306

[56] References Cited

U.S. PATENT DOCUMENTS

| | | | |
|---|---|---|---|
| 2,817,336 | 12/1957 | Kravitz et al. | 128/253 |
| 3,580,254 | 5/1971 | Stuart | 128/268 |
| 4,018,357 | 4/1977 | Ostrem | 222/81 |
| 4,117,841 | 10/1978 | Perotta et al. | 128/155 |
| 4,693,711 | 9/1987 | Bremer et al. | 604/306 |
| 4,808,172 | 2/1989 | Murata et al. | 128/155 |

FOREIGN PATENT DOCUMENTS

| | | | |
|---|---|---|---|
| 0144891 | 6/1985 | European Pat. Off. | A61F 13/02 |
| 3721595A1 | 1/1988 | Germany | A61F 13/02 |
| 9100548 | 10/1992 | Netherlands | A61L 15/58 |

*Primary Examiner*—Edward J. Webman
*Attorney, Agent, or Firm*—Webb Ziesenheim Bruening Logsdon Orkin & Hanson, P.C.

[57] ABSTRACT

A plaster having a porous cushion and at least one adhesive edge with which the plaster can adhere to the skin. The plaster has a capsule closed by a breakable membrane adjacent the cushion. A supply of a medically active substance is contained within the capsule. By breaking the membrane, the medically active substance can be absorbed into the cushion for contact with and gradual delivery to the skin. The plaster further includes a breaking assembly for breaking the membrane. The breaking assembly includes two plates adjacent to the membrane which are adjoined by at least partially complementary edges. The plates can be pressed toward one another by a user, whereby the plates hinge relative to the complementary edges and at least one of the complementary edges breaks the membrane.

9 Claims, 2 Drawing Sheets

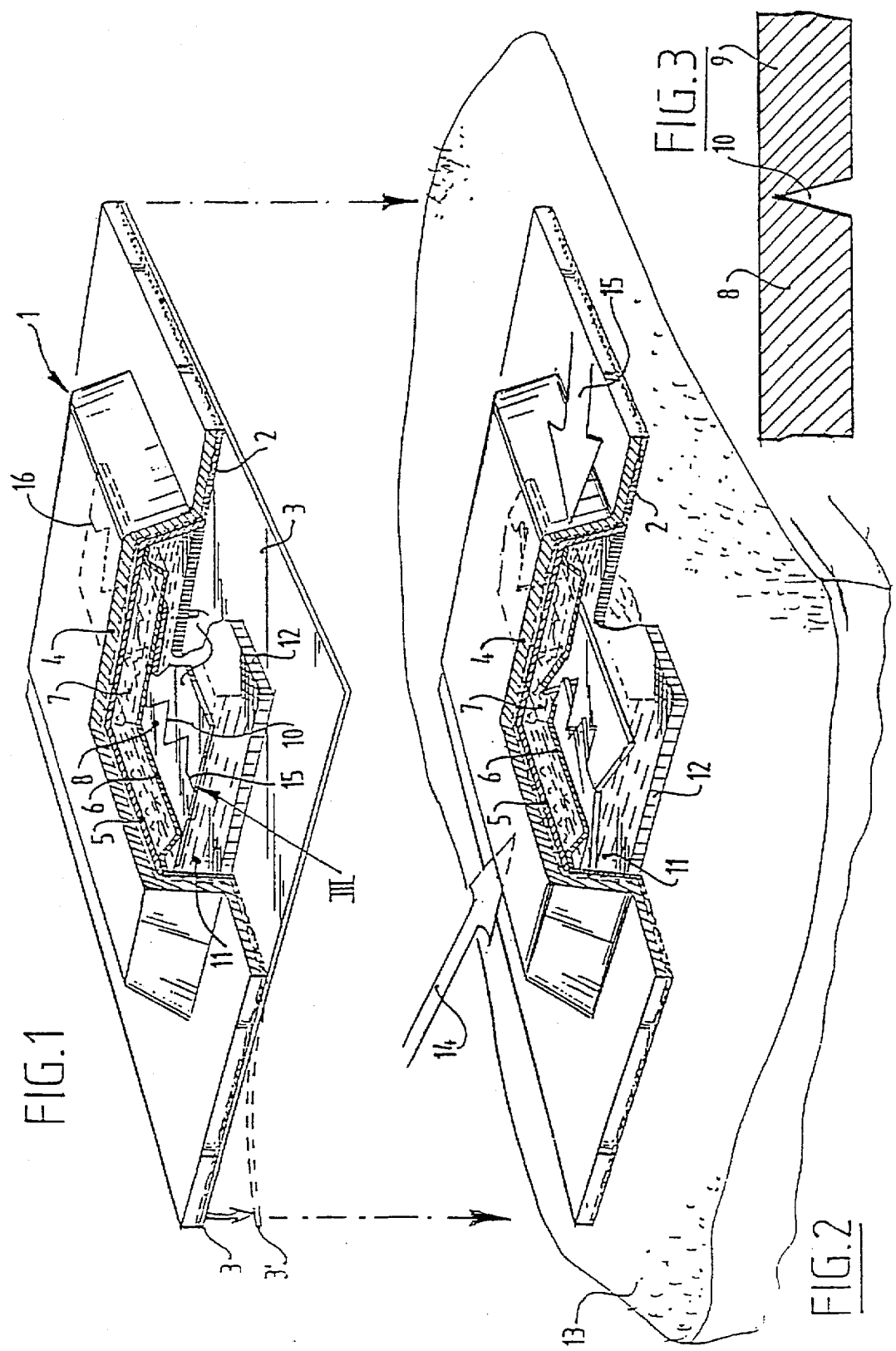

PLASTER WITH A SUPPLY OF A MEDICALLY ACTIVE SUBSTANCE

FIELD OF THE INVENTION

This is a National Stage Application under 35 USC 371 of PCT/NL/00216, filed Oct. 26, 1993.

The invention relates to a plaster, comprising:

a porous cushion and at least one adhesive edge with which the plaster can adhere to the skin, a capsule closed by a breakable membrane and adjoining the cushion via that membrane, for example at least partially embedded therein, in which capsule a supply of a medically active substance is contained which, through breaking of the membrane, can be absorbed into the cushion for contact with and gradual delivery to the skin;

breaking means for breaking the membrane.

BACKGROUND OF THE INVENTION

Such a plaster is known from DE-A-37 21 595. The plaster known from this prior art specification comprises breaking means designed as relatively complicated three-dimensional structures shaped such that by exerting a pressure substantially vertically on the outer surface, a sharp edge forming part of the three-dimensional structure is pressed downward to break a closing membrane, thus releasing the medically active substance from the capsule.

It is a purpose of the invention to embody the plaster such that it does not require the use of relatively complicated three-dimensional structures.

SUMMARY OF THE INVENTION

The present invention comprises a porous cushion and at least one adhesive edge with which the plaster can adhere to the skin;

a capsule closed by a breakable membrane and adjoining the cushion via that membrane, for example at least partially embedded therein, in which capsule a supply of a medically active substance is contained which, through breaking of the membrane, can be absorbed into the cushion for contact with and gradual delivery to the skin; and a breaking means for breaking the membrane.

Thereto the plaster of the invention is characterized in that said breaking means comprise two places adjacent to the membrane and mutually adjoining with at least partially complementary edges, which plates can be pressed toward one another by a user, whereby the plates hinge mutually relative to the edges and at least one of the edges breaks the membrane. It should be noted that the plates define substantially one main plate and do not form part of the capsule itself, contrary to the teachings of DE-A-37 21 595.

After arranging the plaster on the skin through adhesive attachment by means of the adhesive edge, the user can release the medically active substance by pressing the plates toward one another, whereby they undergo a hinge movement and are in a position to break the membrane. Through breaking of this membrane the active substance can be absorbed into the cushion. This cushion can then deliver the substance to the skin.

In order to cause the breaking of the membrane to take place with the greatest possible certainty the plaster can have the feature in a preferred embodiment that at least one of the edges has a sharp protrusion.

In particular this plaster can display the feature that at least one of the edges has a zigzag shape with pointed extremities.

A very practical and simple embodiment, in which the correct mutual positioning of the plates is automatically ensured, is that in which the plates are mutually joined via a weakening line, which weakening line is situated between the complementary edge parts. In this case the weakening line can preferably be embodied such that it is a score line which is situated on the side of the plates remote from the capsule. Thus is additionally ensured, insofar as still necessary, that the hinge movement of the plates of the breaking edges takes place such that the membrane is broken. It is noted that after adhering the plaster to the skin the plates can only move outwardly relative to the skin, namely the direction of the least resistance.

In order to cause the steady dosing of the medically active substance to take place as effectively as possible a particular embodiment is characterized by a gauze extending over the free surface of the cushion to be directed towards the skin. This gauze encloses spaces in which the medically active substance can be temporarily stored in order to be delivered gradually to the skin. Depending on the application of the plaster it can be recommended to choose for this gauze a material which does not adhere to the skin or to a wound. Polypropylene for example can be a suitable choice.

The invention will now be elucidated with reference to the annexed drawings.

BRIEF DESCRIPTION OF THE DRAWINGS

FIG. 1 shows a highly schematic, partially broken away perspective view of a plaster according to the invention;

FIG. 2 shows the plaster of FIG. 1 in the situation in which it is arranged on the skin and the breaking plates are tilted relative to one another;

FIG. 3 shows a cross section through the detail III in FIG 1; and

DESCRIPTION OF THE PREFERRED EMBODIMENTS

Figure 4:
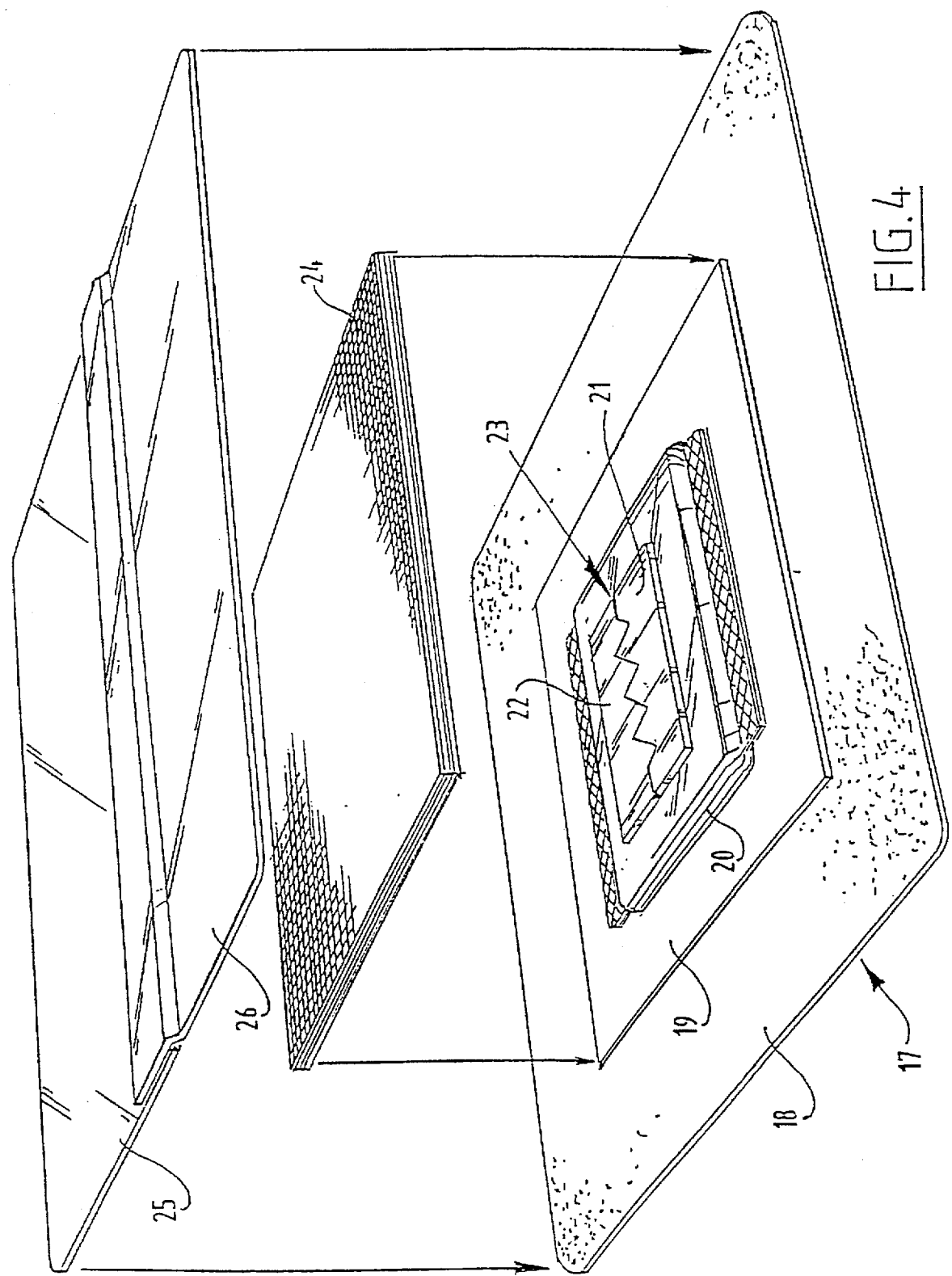
FIG. 4 shows an exploded view of a variant.

FIG. 1 shows a plaster 1 according to the invention. Via an adhesive layer 2 the plaster is covered on its side to be directed toward the skin by means of a silicone-based protective foil 3 This protective foil is removed prior to adhering of the plaster 1 to the skin.

The adhesive layer 2 is attached to a support layer of spun-laced hydrophobic polyester. In the middle of the adhesive layer 2 a polyethylene film 5 is attached thereto. Together with a breakable membrane 6 the film 5 encloses a capsule which contains a medically active substance 7. Situated under the capsule 5, 6 are two breaking plates 8, 9 formed integrally and thus connected to one another, which are mutually joined by means of a zigzag score line 10. Extending thereunder is a porous cushion 11 covered on the underside by means of a gauze 12.

FIG. 2 shows the situation in which the plaster 1, after removal of the protective foil 3, is arranged adheringly on the skin 13. The user can now break the score line 10 by exerting a pressure force according to the arrows 14, 15, whereby the breaking plates 8, 9 hinge relative to one another as is shown clearly in FIG. 2. The zigzag shape of the score line 10 ensures that the breaking plates thus have sharp edges, which break the membrane 6 so that the substance 7 can be supplied to the porous-cushion 11.

It is noted here that other shapes of the score line may also be suitable. The use of a weakening line in two plates consisting of one whole has the advantage that such an embodiment excludes the danger of the breaking plates breaking the membrane during transport or incorrect handling. For the hinge movement shown in FIG. 2 it can be desirable that in the score line is also found at least one straight portion which defines the hinge line. Use can also be made here of an embodiment wherein this straight portion, in the plaster 1 two straight portions 15, 16, remain mutually joined and the remaining part, in this case the zigzag part, is already embodied during production such that the edges are mutually separate there, or are mutually joined very weakly.

It will be apparent in this context that diverse variants fall within the scope of the invention.

The gauze 12 can on the one hand serve to prevent adhesion of the cushion 2 to the skin or the wound, but has on the other hand the important function of being able to dose the active substance in a steady and controlled manner. Gauze is very suitable for such a function. The free spaces present therein permit a temporary storage of the medically active substance.

FIG. 3 shows by way of example a form of the score line 10 at the location of the straight portion 15. It is noted that the score line can also be situated on two sides, wherein for example the score line on the top side is less deep and has a more acute top angle than the score line on the underside. Such a structure can also contribute to absolute certainty that the breaking edges move away from the skin toward the membrane 6.

Finally, FIG. 4 shows an alternative embodiment of the plaster according to the invention.

The plaster 17 comprises a number of components which for the sake of clarity are shown here at some mutual distance. A support is embodied in hydrophobic polyester with an adhesive layer 18. The layer is preferably microporous. The adhesive layer is preferably embodied in known manner in hypo-allergenic, acrylic-based material. For a very sensitive skin use can be made of an acrylic lacquer.

The reference numeral 19 refers to a covering film consisting of polyurethane. Situated thereabove is a capsule 20 in which a medically active jelly is contained. Above this is situated a breaking plate consisting of two breaking plate parts 21 and 22 which are mutually separated by a separating zone 23. This separating zone 23 comprises two weakening lines located at a mutual distance which together form a hinge line, between which weakening lines extend a zigzag shape. At the location of this zigzag shape the two plates are mutually separated. The breaking plate 21 can be manufactured for example by plastic injection moulding. At the position of the zigzag shape the membrane of the adjoining part of the capsule 20 is adhered to the breaking plate parts 21 and 22.

A wound cushion 24 extends with the dimensions of the covering film 19 above the breaking plate 21. This wound cushion is suitable for absorbing the medically active jelly. The whole plaster is covered for storage and transport by two overlapping protective foils 25, and 26 which can be removed prior to use.

The plaster according to the invention offers a very high degree of certainty of the foil not being perforated unintentionally. The user must consciously exert a specific force on the plaster in order to break the foil and cause the active substance to be absorbed into the wound cushion. There is no danger of this happening during storage, transport and while the user carries this plaster with him.

I claim:

1. A plaster, comprising:

a porous cushion and at least one adhesive edge with which the plaster can adhere to the skin;

a capsule closed by a breakable membrane and adjoining the cushion via the membrane, in which capsule a supply of a medically active substance is contained which, through breaking of the membrane, can be absorbed into the cushion for contact with and gradual delivery to the skin; and breaking means for breaking the membrane, wherein the breaking means comprise two plates adjacent to the membrane and mutually adjoining with at least partially complementary edges, which plates can be pressed toward one another by a user, whereby the plates hinge relative to the at least partially complementary edges and at least one of the at least partially complementary edges breaks the membrane, and wherein the two plates lie substantially in one plane prior to breaking of the membrane.

2. The plaster of claim 1, wherein said capsule is partially embedded in said cushion.

3. The plaster as claimed in claim 1, wherein at least one of the at least partially complementary edges has a sharp protrusion.

4. The plaster as claimed in claim 3, wherein the at least partially complementary edges have a zigzag shape with pointed extremities.

5. The plaster as claimed in claim 4, wherein the plates are connected via two weakening lines lying at a mutual distance which together form a hinge line, between which weakening lines the zigzag shape extends, and wherein in a region of the zigzag shape the two plates are mutually separated.

6. The plaster as claimed in claim 3, wherein the membrane is adhered to the plates in the region of the sharp protrusion.

7. The plaster as claimed in claim 1, wherein the plates are mutually joined via a weakening line, which weakening line is situated between the at least partially complementary edges.

8. The plaster as claimed in claim 7, wherein the plates are connected via two weakening lines lying at a mutual distance which together form a hinge line, between which weakening lines a zigzag shape extends, and wherein in a region of the zigzag shape the two plates are mutually separated.

9. The plaster as claimed in claim 1, further comprising a gauze extending over a free surface of the cushion to be directed toward the skin.

* * * * *